United States Patent
Ozawa et al.

(10) Patent No.: US 11,319,404 B2
(45) Date of Patent: May 3, 2022

(54) EPOXY COMPOUND, EPOXY RESIN, EPOXY RESIN COMPOSITION, CURED RESIN PRODUCT, PREPREG, FIBER-REINFORCED COMPOSITE MATERIAL, AND PRODUCTION METHODS FOR THESE

(71) Applicant: Teijin Limited, Osaka (JP)

(72) Inventors: Suguru Ozawa, Osaka (JP); Akimichi Oda, Osaka (JP); Hideaki Tominaga, Osaka (JP); Hiroaki Kuwahara, Osaka (JP)

(73) Assignee: TEIJIN LIMITED, Osaka (JP)

( * ) Notice: Subject to any disclaimer, the term of this patent is extended or adjusted under 35 U.S.C. 154(b) by 0 days.

(21) Appl. No.: 17/266,209

(22) PCT Filed: Aug. 7, 2019

(86) PCT No.: PCT/JP2019/031071
§ 371 (c)(1),
(2) Date: Feb. 5, 2021

(87) PCT Pub. No.: WO2020/032090
PCT Pub. Date: Feb. 13, 2020

(65) Prior Publication Data
US 2021/0292471 A1 Sep. 23, 2021

(30) Foreign Application Priority Data
Aug. 8, 2018 (JP) .............................. JP2018-148952

(51) Int. Cl.
| | |
|---|---|
| *C08G 59/32* | (2006.01) |
| *C08L 63/00* | (2006.01) |
| *C07D 303/36* | (2006.01) |
| *C08J 5/24* | (2006.01) |
| *B32B 27/38* | (2006.01) |
| *C08G 59/50* | (2006.01) |
| *C08J 5/04* | (2006.01) |

(52) U.S. Cl.
CPC ....... *C08G 59/3227* (2013.01); *C07D 303/36* (2013.01); *C08G 59/504* (2013.01); *C08J 5/042* (2013.01); *C08J 5/243* (2021.05); *C08J 2363/00* (2013.01)

(58) Field of Classification Search
None
See application file for complete search history.

(56) References Cited

U.S. PATENT DOCUMENTS

| | | | | |
|---|---|---|---|---|
| 4,255,310 | A * | 3/1981 | Oppenlaender | C09D 5/024 524/109 |
| 4,518,786 | A * | 5/1985 | Wang | C07D 207/404 528/321 |
| 2006/0035088 | A1 | 2/2006 | Takano et al. | |
| 2013/0005855 | A1 | 1/2013 | Arai et al. | |
| 2019/0248953 | A1* | 8/2019 | Christensen | C07D 407/12 |

FOREIGN PATENT DOCUMENTS

| | | |
|---|---|---|
| CN | 105294609 A | 2/2016 |
| JP | 02-169618 A | 6/1990 |
| JP | 2005-213352 A | 8/2005 |
| JP | 2009-292976 A | 12/2009 |
| JP | 2009-292977 A | 12/2009 |
| JP | 2010-248379 A | 11/2010 |
| JP | 2011-190430 A | 9/2011 |
| WO | 2004/048435 A1 | 6/2004 |
| WO | 2011/118106 A1 | 9/2011 |
| WO | WO-2013021851 A1 * | 2/2013 ........... C07D 301/27 |

OTHER PUBLICATIONS

Siddiqi, H. M. et al., "Thermally stable epoxy polymers from new tetraglycidyl amine-based resin", Journal of Thermal Analysis and Calorimetry, Jan. 10, 2018, pp. 205-214, vol. 132.
International Search Report of PCT/JP2019/031071 dated Oct. 29, 2019 [PCT/ISA/210].

\* cited by examiner

*Primary Examiner* — Michael J Feely
(74) *Attorney, Agent, or Firm* — Sughrue Mion, PLLC

(57) ABSTRACT

The present invention provides an epoxy compound indicated by chemical formula (1) (in chemical formula (1), X indicates a C1-10 aliphatic hydrocarbon group, $R_1$ and $R_2$ each independently indicate one selected from the group consisting of a hydrogen atom, an aliphatic hydrocarbon group, an aromatic group, an alkoxy group, and a halogen atom)

Chemical Formula (1)

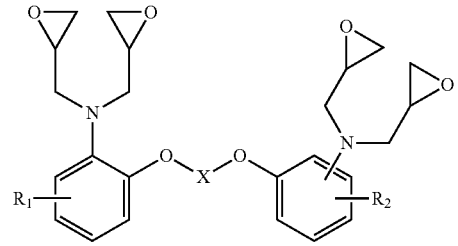

13 Claims, No Drawings

EPOXY COMPOUND, EPOXY RESIN, EPOXY RESIN COMPOSITION, CURED RESIN PRODUCT, PREPREG, FIBER-REINFORCED COMPOSITE MATERIAL, AND PRODUCTION METHODS FOR THESE

CROSS REFERENCE TO RELATED APPLICATIONS

This application is a National Stage of International Application No. PCT/JP2019/031071 filed on Aug. 7, 2019, claiming priority based on Japanese Patent Application No. 2018-148952 filed on Aug. 8, 2018.

TECHNICAL FIELD

The present invention relates to an epoxy compound, an epoxy resin, an epoxy resin composition, a prepreg, a fiber-reinforced composite material, and production methods for these. More specifically, the present invention relates to an epoxy compound having a novel structure; an epoxy, resin containing this epoxy compound; an epoxy resin composition containing this epoxy compound; a cured resin product obtained by curing this epoxy resin composition; a prepreg containing this epoxy resin composition; and a fiber-reinforced composite material containing this cured resin product.

BACKGROUND ART

Epoxy compounds are widely used as raw materials for pharmaceuticals, resins, paints and the like. In particular, an epoxy compound having a plurality of epoxy Groups is cured by reacting with an appropriate curing agent to form a cured resin product having excellent heat resistance, chemical resistance, mechanical properties and the like. Therefore, in particular, it is widely used as a matrix resin for a fiber-reinforced composite material (FRP).

The fiber-reinforced composite material is lightweight and has high strength and high rigidity, and thus is used in a wide range of fields such as sports/leisure applications such as fishing rods and golf shafts, and industrial applications such as automobiles and aircraft. As a method for molding a composite material containing an epoxy resin as a matrix resin, there is a method for molding a prepreg (intermediate base material) formed into a sheet by impregnating reinforcing material fibers with a resin in advance. Other molding methods include a resin transfer molding (RTM) method in which a liquid resin composition is impregnated into a reinforcing fiber base material placed in a mold, and cured to form a fiber-reinforced composite material.

In the production of FRP, a method of using an intermediate material (prepreg) in which a fiber reinforcing material layer made of long fibers such as reinforcing fibers is impregnated with a resin is suitably used. A molded product made of FRP can be obtained by cutting the prepreg into a desired shape, shaping it, and curing it under heat and pressure.

Materials used in the aircraft field are required to have high mechanical properties such as heat resistance and impact resistance. In general, a prepreg using an epoxy resin can provide a molded product having high mechanical properties. However, the prepreg using an epoxy resin requires a long molding time. Further, the molded product obtained by curing the prepreg using an epoxy resin has insufficient water absorption resistance, and the mechanical properties such as heat resistance and impact resistance may be deteriorated during water absorption.

In press molding which enables short-time molding, high-temperature and high-pressure conditions of 100 to 150° C. and 1 to 15 MPa are usually used (Patent Literature 1). The high-temperature and high-pressure conditions can shorten the curing time of the resin constituting the prepreg. In addition, the gas contained in the prepreg can be discharged by appropriately flowing the resin constituting the prepreg in the mold. However, when press molding is performed under the high-temperature and high-pressure conditions, the temperature of the resin constituting the prepreg rises and the resin viscosity decreases remarkably. As a result, depending on the structure of the mold, the resin flows out violently from the shear edge portion (hereinafter, the phenomenon that the resin flows out from the prepreg due to heating and pressurization in the molding process is referred to also as "resin flow"). Therefore, the obtained FRP has poor appearance such as unimpregnated portions of the resin composition (resin withering) and fiber meandering, and poor performance due to these.

Patent Literature 2 describes a method of using a high-viscosity epoxy resin or adding a thermoplastic: resin to an epoxy resin as a method for suppressing a resin flow. However, when a high-viscosity epoxy resin is used, the resin viscosity at room temperature (25° C.) also in Therefore, the handleability of the prepreg is extremely low, for example, the laminating operation becomes difficult.

Patent Literatures 3 to 5 each describe a prepreg for high-cycle press molding that is improved in handleability at room temperature and suppresses a resin flow without lowering of the glass transition temperature (Tg) or the curing rate. The resin used in each of the prepregs described in Patent Literatures 3 to 5 is a resin in which the resin viscosity is increased by dissolving a thermoplastic resin in a liquid epoxy resin. However, since the resin viscosity during the production of a prepreg is also high, the impregnation property of the resin into the reinforcing fiber base material layer is lowered, and voids may be generated in the FRP after molding.

In the field of aircraft, mechanical properties such as high heat resistance and impact resistance are required, and various methods have been proposed for the purpose of improving impact resistance and interlayer toughness. In particular, many methods have been proposed in which a material different from the matrix resin is placed between layers to absorb fracture energy (Patent Literature 6) However, the curing time of the resin generally takes 120 minutes or more, and it is difficult to perform short-time molding.

Further, Patent Literatures 1 to 6 nowhere mention the water absorption resistance of the obtained FRP.

CITATION LIST

Patent Literature

Patent Literature 1: WO 2004/48435
Patent Literature 2: JP 2005-213352 A
Patent Literature 3: JP 2009-292976 A
Patent Literature 4: JP 2009-292977 A
Patent Literature 5: JP 2010-248379 A
Patent Literature 6: JP 2011-190430 A.

SUMMARY OF INVENTION

Technical Problem

An object of the present invention is to solve the above-described problems of the prior art, and to provide an epoxy compound that enables production of a cured resin product having high water absorption resistance and a high elastic modulus, and has high impregnation property into a reinforcing fiber base material and excellent handleability. A further object of the present invention is to provide an epoxy resin composition, a prepreg, and a fiber-reinforced composite material, utilizing this epoxy compound (hereinafter, sometimes abbreviated as "FRP"; in particular, when the reinforcing fiber base material is carbon fiber, sometimes abbreviated as "CFRP").

Solution to Problem

As a result of studies to solve the above problems, the present inventors have found that the above problems can be solved by using an epoxy compound having a predetermined structure, and have completed the present invention.

The present invention that achieves the above problems is as described below.

[1] An epoxy compound represented by the following chemical formula (1):

[Chemical Formula 1]

Chemical Formula (1)

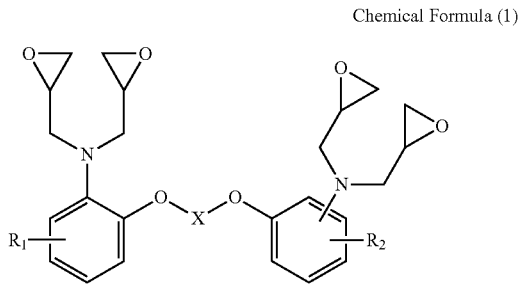

wherein X represents a C1-10 aliphatic hydrocarbon group, and $R_1$ and $R_2$ each independently represent one selected from the group consisting of a hydrogen atom, an aliphatic hydrocarbon group, an aromatic group, an alkoxy Group, and a halogen atom.

[2] The epoxy compound according to [1], which is represented by the following chemical formula (2)

[Chemical Formula 2]

Chemical Formula (2)

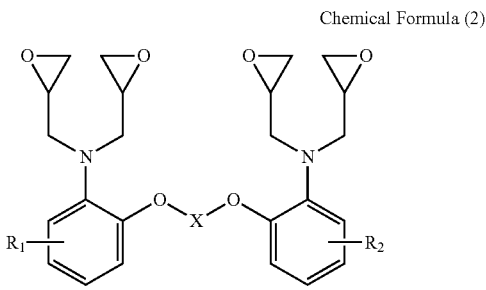

wherein X represents a C1-10 aliphatic hydrocarbon Group, and $R_1$ and $R_2$ each independently represent one selected from the group consisting of a hydrogen atom, an aliphatic hydrocarbon group, an aromatic group, an alkoxy group, and a halogen atom.

[3] The epoxy compound according to [1] or [2], wherein X is a linear aliphatic chain group.

The inventions according to [1] to [3] are each directed to as epoxy compound having a predetermined structure. In the respective chemical formulas, X is preferably a linear aliphatic chain group.

[4] An epoxy resin containing the epoxy compound according to any one of [1] to [3] in an area ratio of 50% or more in HPLC measurement.

The invention according to [4] is directed to an epoxy resin containing the epoxy compound having a predetermined structure in a predetermined amount. This epoxy resin may only contain the epoxy compound according to [1] to [3] in a predetermined ratio, and the epoxy compound according to [1] to [3] does not necessarily have to be isolated.

[5] An epoxy resin composition containing at least:
the epoxy compound according to any one of [1] to [3]; and
a curing agent.

The invention according to [5] is directed to a composition in an uncured or semi-cured state, which contains at least the epoxy compound according to [1] to [3]; and a curing agent that reacts with the epoxy compound.

[6] A cured resin product obtained by curing the epoxy resin composition according to [5].

The invention according to [6] is directed to a cured resin product obtained after a curing reaction of the epoxy resin composition according to [5].

[7] A prepreg including:
a reinforcing fiber base material; and
the epoxy resin composition according to [5], which is impregnated into the reinforcing fiber base material.

[8] The prepreg according to [7], wherein the reinforcing fiber base material is a reinforcing fiber base material made of carbon fibers.

[9] A method for producing the prepreg according to [7], including impregnating the epoxy resin composition into the reinforcing fiber base material.

The inventions according to [7] to [9] are directed to a prepreg containing a reinforcing fiber base material and an epoxy resin composition impregnated into the reinforcing fiber base material, and a method for producing the same.

[10] A fiber-reinforced composite material containing:
the cured resin product according to [6]; and
a reinforcing fiber base material.

[11] A method for producing the fiber-reinforced composite material according to [10], including impregnating the epoxy resin composition according to [5] into the reinforcing fiber base material and curing the epoxy resin composition.

[12] A method for producing the fiber-reinforced composite material according to [10], including curing the prepreg according to [7] or [8].

The inventions according to [10] to [12] are directed to a fiber-reinforced composite material containing the cured resin product of the present invention and a reinforcing fiber base material, and a method for producing the same. The reinforcing fiber base material and the epoxy resin composition may be composited in advance, and then the resultant product (prepreg) is molded. Further, the reinforcing fiber base material and the cured resin may be molded and composited at the same time, not via formation of a prepreg.

Advantageous Effects of Invention

The epoxy resin composition containing the epoxy compound of the present invention enables production of a cured resin product having a high elastic modulus and high water absorption resistance. Further, the epoxy resin composition of the present invention has a low viscosity, and thus has high impregnation property into the reinforcing fiber base material and high handleability.

DESCRIPTION OF EMBODIMENTS

Hereinafter, the epoxy compound, epoxy, resin, epoxy resin composition, prepreg and fiber-reinforced composite material of the present invention, and the production methods for these will be described.

The epoxy compound as used herein means a compound itself represented by each chemical formula. Further, the epoxy resin means a mixture containing the epoxy compound. That is, the epoxy resin may contain various by-products and unreacted products produced during the synthesis of the epoxy compound. The epoxy resin composition means a composition in an uncured or semi-cured state, which contains at least the epoxy compound and a curing agent therefor. The cured resin product (hereinafter, also referred to as "cured resin") means a cured product obtained by a curing reaction of the epoxy resin composition.

1. Epoxy Compound

The epoxy compound of the present invention is an epoxy compound represented by the following chemical formula (1).

This epoxy compound is composed of two aromatic rings having a diglycidylamine and an ether bond, which aromatic rings are bonded via an aliphatic hydrocarbon, and characterized in that the ether bond and the glycidylamine are present at the ortho position in at least one aromatic ring. The present inventors presume that the elastic modulus and water absorption resistance of the cured resin increase due to the special steric structure of the cured resin generated by this structure.

[Chemical Formula 3]

Chemical Formula (1)

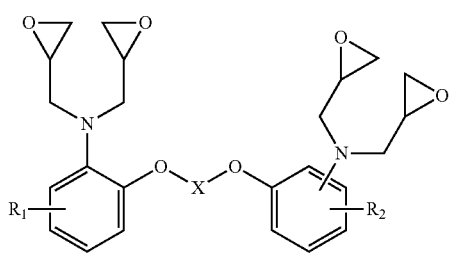

wherein X represents a C1-10 aliphatic hydrocarbon group, and $R_1$ and $R_2$ each independently represent one selected from the group consisting of a hydrogen atom, an aliphatic hydrocarbon group, an aromatic group, as alkoxy group, and a halogen atom.

Among the compounds represented by the above chemical formula (1), the epoxy compound represented by the following chemical formula (2) is particularly preferable.

[Chemical Formula 4]

Chemical Formula (2)

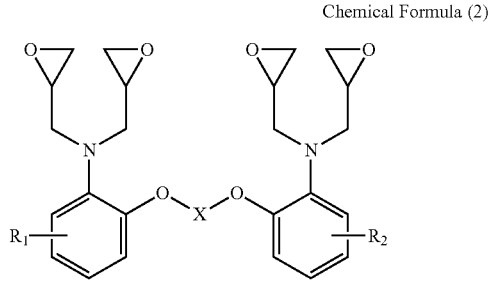

X in the above chemical formula (1) or (2) is not particularly limited as long as it is an aliphatic hydrocarbon group, such as a linear aliphatic chain group, a branched-chain aliphatic hydrocarbon group, and an alicyclic hydrocarbon group. A linear aliphatic chain group is preferable. Further, it may be a saturated aliphatic hydrocarbon group or an unsaturated aliphatic hydrocarbon Group, but a saturated aliphatic hydrocarbon group is more preferable.

The carbon number of X in the above chemical formula (1) or (2) is preferably 1 to 8, more preferably 1 to 6, further preferably 2 to 4.

$R_1$ and $R_2$ in the above chemical formula (1) or (2) are each independently preferably a hydrogen atom, a C1-4 aliphatic hydrocarbon group, an aromatic group, a C1-4 alkoxy group or a halogen atom, more preferably a hydrogen atom or a C1-4 aliphatic hydrocarbon group.

The epoxy compound of the present invention preferably has a viscosity at 30° C. of less than 50 Pa·s, more preferably less than 10 Pa·s, further preferably less than 5.0 Pa·s, particularly preferably less than 2.0 Pas.

Examples of such epoxy compounds include compounds having the following chemical formulas (3) and (4).

[Chemical Formula 5]

Chemical Formula (3)

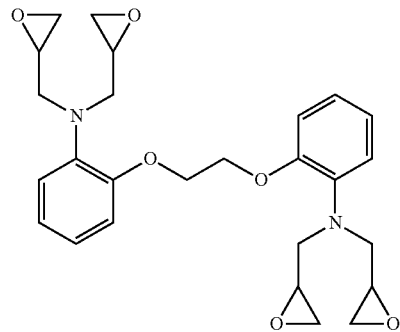

[Chemical Formula 6]

Chemical Formula (4)

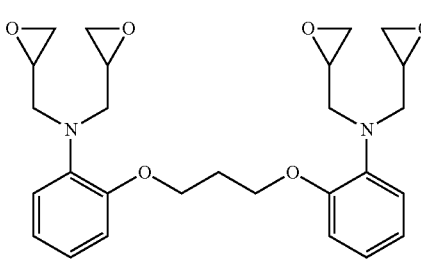

Such an epoxy compound may be synthesized by any method. For example, such an epoxy compound is obtained by reacting an aromatic diamine compound as a raw material and epihalohydrin such as epichlorohydrin in the presence of an acid catalyst to form tetrahalohydrin, and subjecting the tetrahalohydrin to a cyclization reaction using as alkaline compound. More specifically, it can be synthesized by the method of Examples which will be described later.

As the raw material aromatic diamine, any aromatic diamine can be employed as long as two aromatic rings each having an amine and an ether bond are bonded via an aliphatic hydrocarbon, and the ether bond and the amine are present at the ortho position in at least one aromatic ring.

Examples of aromatic diamines in which the aliphatic hydrocarbon is a C1 aliphatic hydrocarbon include 1,1-bis(2-aminophenoxy)methane, 1-(2-aminophenoxy)-1-(2-amino-3-methylphenoxy)methane, 1-(2-aminophenoxy)-1-(3-aminophenoxy)methane, 1-(2-aminophenoxy)-1-(3-amino-2-methylphenoxy)methane, 1-(2-aminophenoxy)-1-(3-amino-4-methylphenoxy)methane, 1-(2-aminophenoxy)-1-(4-aminophenoxy) methane, 1-(2-aminophenoxy)-1-(4-amino-3-methylphenoxy)methane, 1,1-bis(2-amino-3-methylphenoxy)methane, 1-(2-amino-3-methylphenoxy)-1-(3-aminophenoxy)methane, 1-(2-amino-3-methylphenoxy)-1-(3-amino-2-methylphenoxy)methane, 1-(2-amino-3-methylphenoxy)-1-(3-amino-4-methylphenoxy)methane, 1-(2-amino-3-methylphenoxy)-1-(4-aminophenoxy)methane, and 1-(2-amino-3-methylphenoxy)-1-(4-amino-3-methylphenoxy)methane.

Examples of aromatic diamines in which the aliphatic hydrocarbon is a C2 aliphatic hydrocarbon include 1,2-bis(2-aminophenoxy)ethane, 1-(2-aminophenoxy)-2-(2-amino-3-methylphenoxy)ethane, 1-(2-aminophenoxy)-2-(3-aminophenoxy)ethane, 1-(2-aminophenoxy)-2-(3-amino-2-methylphenoxy)ethane, 1-(2-aminophenoxy)-2-(3-amino-4-methylphenoxy)ethane, 1-(2-aminophenoxy)-2-(4-aminophenoxy)ethane, 1-(2-aminophenoxy)-2-(4-amino-3-methylphenoxy)ethane, 1,2-bis(2-amino-3-methylphenoxy)ethane, 1-(2-amino-3-methylphenoxy)-2-(3-aminophenoxy)ethane, 1-(2-amino-3-methylphenoxy)-2-(3-amino-2-methylphenoxy)ethane, 1-(2-amino-3-methylphenoxy)-2-(3-amino-4-methylphenoxy)ethane, 1-(2-amino-3-methylphenoxy)-2-(4-aminophenoxy)ethane, and 1-(2-amino-3-methylphenoxy)-2-(4-amino-3-methylphenoxy) ethane.

Examples of aromatic diamines in which the aliphatic hydrocarbon is a C3 aliphatic hydrocarbon include 1,3-bis(2-aminophenoxy)propane, 1-(2-aminophenoxy)-3-(2-amino-3-methylphenoxy)propane, 1-(2-aminophenoxy)-3-(3-aminophenoxy) propane, 1-(2-aminophenoxy)-3-(3-amino-2-methylphenoxy)propane, 1-(2-aminophenoxy)-3-(3-amino-4-methylphenoxy)propane, 1-(2-aminophenoxy)-3-(4-aminophenoxy)propane, 1-(2-aminophenoxy)-3-(4-amino-3-methylphenoxy)propane, 1,3-bis(2-amino-3-methylphenoxy)propane, 1-(2-amino-3-methylphenoxy)-3-(3-aminophenoxy)propane, 1-(2-amino-3-methylphenoxy)-3-(3-amino-2-methylphenoxy)propane, 1-(2-amino-3-methylphenoxy)-3-(3-amino-4-methylphenoxy)propane, 1-(2-amino-3-methylphenoxy)-3-(4-aminophenoxy)propane, and 1-(2-amino-3-methylphenoxy)-3-(4-amino-3-methylphenoxy)propane.

Examples of aromatic diamines in which the aliphatic hydrocarbon is a C4 aliphatic hydrocarbon include 1,4-bis(2-aminophenoxy)butane, 1-(2-aminophenoxy)-4-(2-amino-3-methylphenoxy)butane, 1-(2-aminophenoxy)-4-(3-aminophenoxy)butane, 1-(2-aminophenoxy)-4-(3-amino-2-methylphenoxy)butane, 1-(2-aminophenoxy)-4-(3-amino-4-methylphenoxy)butane, 1-(2-aminophenoxy)-4-(4-aminophenoxy)butane, 1-(2-aminophenoxy)-4-(4-amino-3-methylphenoxy)butane, 1,4-bis(2-amino-3-methylphenoxy)butane, 1-(2-amino-3-methylphenoxy)-4-(3-aminophenoxy)butane, 1-(2-amino-3-methylphenoxy)-4-(3-amino-2-methylphenoxy)butane, 1-(2-amino-3-methylphenoxy)-4-(3-amino-4-methylphenoxy)butane, 1-(2-amino-3-methylphenoxy)-4-(4-aminophenoxy)butane, and 1-(2-amino-3-methylphenoxy)-4-(4-amino-3-methylphenoxy) butane.

Examples of aromatic diamines in which the aliphatic hydrocarbon is a C5 aliphatic hydrocarbon include 1,5-bis(2-aminophenoxy)pentane, 1-(2-aminophenoxy)-5-(2-amino-3-methylphenoxy)pentane, 1-(2-aminophenoxy)-5-(3-aminophenoxy)pentane, 1-(2-aminophenoxy)-5-(3-amino-2-methylphenoxy)pentane, 1-(2-aminophenoxy)-5-(3-amino-4-methylphenoxy)pentane, 1-(2-aminophenoxy)-5-(4-aminophenoxy)pentane, 1-(2-aminophenoxy)-5-(4-amino-3-methylphenoxy)pentane, 1,5-bis(2-amino-3-methylphenoxy)pentane, 1-(2-amino-3-methylphenoxy)-5-(3-aminophenoxy)pentane, 1-(2-amino-3-methylphenoxy)-5-(3-amino-2-methylphenoxy)pentane, 1-(2-amino-3-methylphenoxy)-5-(3-amino-4-methylphenoxy)pentane, 1-(2-amino-3-methylphenoxy)-5-(4-aminophenoxy)pentane, and 1-(2-amino-3-methylphenoxy)-5-(4-amino-3-methylphenoxy)pentane.

Examples of aromatic diamines in which the aliphatic hydrocarbon is a C6 aliphatic hydrocarbon include 1,6-bis(2-aminophenoxy)hexane, 1-(2-aminophenoxy)-6-(2-amino-3-methylphenoxy)hexane, 1-(2-aminophenoxy)-6-(3-aminophenoxy)hexane, 1-(2-aminophenoxy)-6-(3-amino-2-methylphenoxy)hexane, I-(2-aminophenoxy)-6-(3-amino-4-methylphenoxy)hexane, 1-(2-aminophenoxy)-6-(4-aminophenoxy)hexane, 1-(2-aminophenoxy)-6-(4-amino-3-methylphenoxy)hexane, 1,6-bis(2-amino-3-methylphenoxy)hexane, 1-(2-amino-3-methylphenoxy)-6-(3-aminophenoxy)hexane 1-(2-amino-3-methylphenoxy)-6-(3-amino-2-methylphenoxy)hexane, 1-(2-amino-3-methylphenoxy)-6-(3-amino-4-methylphenoxy)hexane, 1-(2-amino-3-methylphenoxy)-6-(4-aminophenoxy)hexane, and 1-(2-amino-3-methylphenoxy)-6-(4-amino-3-methylphenoxy)hexane.

Examples of aromatic diamines in which the aliphatic hydrocarbon is a C7 aliphatic hydrocarbon include 1,7-bis(2-aminophenoxy)heptane, 1-(2-aminophenoxy)-7-(2-amino-3-methylphenoxy)heptane, (2-aminophenoxy)-7-(3-aminophenoxy)heptane, 1-(2-aminophenoxy)-7-(3-amino-2-methylphenoxy)heptane, 1-(2-aminophenoxy)-7-(3-amino-4-methylphenoxy)heptane, 1-(2-aminophenoxy)-7-(4-aminophenoxy)heptane, 1-(2-aminophenoxy)-7-(4-amino-3-methylphenoxy)heptane, 1,7-bis(2-amino-3-methylphenoxy)heptane, 1-(2-amino-3-methylphenoxy)-7-(3-aminophenoxy)heptane, (2-amino-3-methylphenoxy)-7-(3-amino-2-methylphenoxy)heptane, (2-amino-3-methylphenoxy)-7-(3-amino-4-methylphenoxy)heptane, 1-(2-amino-3-methylphenoxy)-7-(4-aminophenoxy)heptane, and 1-(2-amino-3-methylphenoxy)-7-(4-amino-3-methylphenoxy)heptane.

Examples of aromatic diamines in which the aliphatic hydrocarbon is a C8 aliphatic hydrocarbon include 1,8-bis(2-aminophenoxy)octane, 1-(2-aminophenoxy)-8-(2-amino-3-methylphenoxy)octane, 1-(2-aminophenoxy)-8-(3-aminophenoxy)octane, 1-(2-aminophenoxy)-8-(3-amino-2-methylphenoxy)octane, 1-(2-aminophenoxy)-8-(3-amino-4-methylphenoxy)octane, 1-(2-aminophenoxy)-8-(4-aminophenoxy)octane, 1-(2-aminophenoxy)-8-(4-amino-3-methylphenoxy)octane, 1,8-bis(2-amino-3-methylphenoxy)

octane, 1-(2-amino-3-methylphenoxy)-8-(3-aminophenoxy) octane, 1-(2-amino-3-methylphenoxy)-8-(3-amino-2-methylphenoxy)octane, 1-(2-amino-3-methylphenoxy)-8-(3-amino-4-methylphenoxy)octane, 1-(2-amino-3-methylphenoxy)-8-(4-aminophenoxy)octane, and 1-(2-amino-3-methylphenoxy)-8-(4-amino-3-methylphenoxy) octane.

Examples of aromatic diamines in which the aliphatic hydrocarbon is a C9 aliphatic hydrocarbon include 1,9-bis(2-aminophenoxy)nonane, 1-(2-aminophenoxy)-9-(2-amino-3-methylphenoxy)nonane, 1-(2-aminophenoxy)-9-(3-aminophenoxy)nonane, 1-(2-aminophenoxy)-9-(3-amino-2-methylphenoxy)nonane, 1-(2-aminophenoxy)-9-(3-amino-4-methylphenoxy)nonane, 1-(2-aminophenoxy)-9-(4-aminophenoxy)nonane, 1-(2-aminophenoxy)-9-(4-amino-3-methylphenoxy)nonane, 1,9-bis(2-amino-3-methylphenoxy)nonane, 1-(2-amino-3-methylphenoxy)-9-(3-aminophenoxy)nonane, 1-(2-amino-3-methylphenoxy)-9-(3-amino-2-methylphenoxy)nonane, 1-(2-amino-3-methylphenoxy)-9-(3-amino-4-methylphenoxy)nonane, 1-(2-amino-3-methylphenoxy)-9-(4-aminophenoxy)nonane, and 1-(2-amino-3-methylphenoxy)-9-(4-amino-3-methylphenoxy)nonane.

Examples of aromatic diamines in which the aliphatic hydrocarbon is a C10 aliphatic hydrocarbon include 1,10-bis(2-aminophenoxy)decane, 1-(2-aminophenoxy)-10-(2-amino-3-methylphenoxy)decane, 1-(2-aminophenoxy)-10-(3-aminophenoxy)decane, 1-(2-aminophenoxy)-10-(3-amino-2-methylphenoxy)decane, 1-(2-aminophenoxy)-10-(3-amino-4-methylphenoxy)decane, 1-(2-aminophenoxy)-10-(4-aminophenoxy)decane, 1-(2-aminophenoxy)-10-(4-amino-3-methylphenoxy)decane, 1,10-bis(2-amino-3-methylphenoxy)decane, 1-(2-amino-3-methylphenoxy)-10-(3-aminophenoxy)decane, 1-(2-amino-3-methylphenoxy)-10-(3-amino-2-methylphenoxy)decane, 1-(2-amino-3-methylphenoxy)-10-(3-amino-4-methylphenoxy)decane, 1-(2-amino-3-methylphenoxy)-10-(4-aminophenoxy)decane, and 1-(2-amino-3-methylphenoxy)-10-(4-amino-3-methylphenoxy)decane.

Examples of aromatic diamines in which the aliphatic hydrocarbon is a cycloaliphatic hydrocarbon include 1,4-bis(2-aminophenoxymethyl)cyclohexane, 1-(2-aminophenoxymethyl)-4-(2-amino-3-methylphenoxymethyl)cyclohexane, 1-(2-aminophenoxymethyl)-4-(3-aminophenoxymethyl)cyclohexane, 1-(2-aminophenoxymethyl)-4-(3-amino-2-methylphenoxymethyl)cyclohexane, 1-(2-aminophenoxymethyl)-4-(3-amino-4-methylphenoxymethyl)cyclohexane, 1-(2-aminophenoxymethyl)-4-(4-aminophenoxymethyl) cyclohexane, 1-(2-aminophenoxymethyl) 4-(4-amino-3-methylphenoxymethyl)cyclohexane, 1,4-bis(2-amino-3-methylphenoxymethyl)cyclohexane, 1-(2-amino-3-methylphenoxymethyl)-4-(3-aminophenoxymethyl) cyclohexane, 1-(2-amino-3-methylphenoxymethyl)-4-(3-amino-2-methylphenoxymethyl)cyclohexane, 1-(2-amino-3-methylphenoxymethyl)-4-(3-amino-4-methylphenoxymethyl)cyclohexane, 1-(2-amino-3-methylphenoxymethyl)-4-(4-aminophenoxymethyl) cyclohexane, and 1-(2-amino-3-methylphenoxymethyl)-4-(4-amino-3-methylphenoxy)cyclohexane.

Examples of the epihalohydrin include epichlorohydrin, epibromohydrin, and epifluorohydrin. Among these, epichlorohydrin and epibromohydrin are particularly preferable from the viewpoint of reactivity and handleability.

The mass ratio of the aromatic diamine to the ephalohydrin is preferably 1:1 to 1:20, more preferably 1:3 to 1:10.

As the solvent used during the reaction, an alcohol solvent such as ethanol or n-butanol; a ketone solvent such as methylisobutylketone or methylethylketone; an aprotic polar solvent such as acetonitrile or N,N-dimethylformamide; and an aromatic hydrocarbon solvent such as toluene or xylene are exemplified. In particular, an alcohol solvent such as ethanol or n-butanol, or an aromatic hydrocarbon solvent such as toluene or xylene is preferable. The amount of the solvent used is preferably 1 to 10 times by mass with respect to the aromatic diamine.

Both Bronsted acid and Lewis acid can be preferably used as the acid catalyst, and ethanol, water or acetic acid is particularly preferable as the Bronsted acid. As the Lewis acid, titanium tetrachloride, lanthanum nitrate hexahydrate, or boron trifluoride diethyl ether complex is preferable.

The reaction time is preferably 0.1 to 180 hours, more preferably 0.5 to 24 hours. The reaction temperature is preferably 20 to 100° C., more preferably 40 to 80° C.

Examples of the alkaline compound used during the cyclization reaction include sodium hydroxide and potassium hydroxide. The alkaline compound may be added as a solid or as an aqueous solution.

A phase transfer catalyst may be used during the cyclization reaction. Examples of the phase transfer catalyst include quaternary ammonium salts such as tetramethylammonium chloride, tetraethylammonium bromide, benzyltriethylammonium chloride, and tetrabutylammonium hydrogensulfate; phosphonium compounds such as tributylhexadecylphosphonium bromide and tributyldodecylphosphonium bromide; and crown ethers such as 18-crown-6-ether.

2. Epoxy Resin

The epoxy compound represented by the above chemical formula (1) does not necessarily have to be isolated after synthesis. It may be used as an epoxy resin containing by-products and unreacted substances produced during the synthesis of the above chemical formula (1). The epoxy resin of the present invention is an epoxy resin containing the epoxy compound represented by the above chemical formula (1) in an area ratio of 50% or more in HPLC measurement. The epoxy resin of the present invention contains the epoxy compound represented by the above chemical formula (1) in an area ratio of preferably 60% or more, more preferably 70% or more, in HPLC measurement. Due to incorporation of the epoxy compound in an area ratio of 50% or more, water absorption resistance and elastic modulus can be increased.

The epoxy resin of the present invention has a viscosity at 50° C. of preferably less than 50 Pa·s, more preferably less than 10 Pa·s, further preferably less than 5.0 Pa·s, particularly preferably less than 2.0 Pa·s.

3. Epoxy Resin Composition

The epoxy resin composition of the present invention is a composition in an uncured or semi-cured state, which contains at least the epoxy compound of the present invention and a curing agent. In addition to these, the epoxy resin composition of the present invention may contain any other thermosetting resin and/or thermoplastic resin, and/or any other additive. Further, in the epoxy resin composition of the present invention, the epoxy compound and the curing agent may only coexist when it is cured. A composition containing an epoxy compound and a curing agent may be prepared in advance according to the molding method used. Further, a composition containing an epoxy compound and a composition containing a curing agent may be prepared separately and mixed, for example, in a molding mold.

The viscosity of the epoxy resin composition of the present invention may only be appropriately adjusted according to the molding method. For example, when it is used as a prepreg, the viscosity at 50° C. is preferably less than 500 Pa·s, more preferably 0.001 to 100 Pa·s. If it exceeds 500 Pa·s, the handleability may decrease. Further, when a prepreg is produced using this epoxy resin composition, an unimpregnated portion is likely to be generated in the prepreg. As a result, voids and the like are likely to be formed in the obtained fiber-reinforced composite material.

The content proportion of the epoxy compound represented by the above chemical formula (1) in the epoxy resin composition of the present invention is preferably 10 to 90% by mass, more preferably 15 to 80% by mass, further preferably 20 to 70% by mass. If it is less than 10% by mass, the handleability of the epoxy resin composition may deteriorate, and the elastic modulus and water absorption resistance of the obtained cured resin may decrease. If it is more than 90% by mass, the molar balance with the curng agent becomes inappropriate, and various properties such as mechanical properties of the cured product may deteriorate.

The curing agent used in the epoxy resin composition of the present invention is a known curing agent that cures the epoxy resin. Any curing agent may be employed as long as it cures the epoxy resin, and the curing agent is appropriately selected depending on the purpose of use or the like.

Specific examples of the curing agent include aliphatic polyamines, aromatic polyamines, aminobenzoic acid esters, acid anhydrides, and latent curing agents such as dicyandiamide.

Latent curing agents such as dicyandiamide are preferable because they provide excellent storage stability of the prepreg.

Aliphatic polyamines are preferable because they have high reactivity and enable a curing reaction at a low temperature. Examples of aliphatic polyamines include 4,4'-diaminodcyclohexylmethane, isophoronediamine, and xylylenediamine.

Aromatic polyamines are preferable because they are excellent in heat resistance and various mechanical properties. Examples of aromatic polyamines include diaminodiphenyl sulfones, diaminodiphenylmethanes, and toluenediamine derivatives. Among them, aromatic diamine compounds such as 4,4'-diaminodiphenyl sulfone, 3,3'-diaminodiphenyl sulfone and 4,4'-diaminodiphenylmethane, and derivatives thereof having a non-reactive substituent are more preferable because a cured product having high heat resistance can be obtained. In particular, 3,3'-diaminodiphenyl sulfone is further preferable because the obtained cured resin product has high heat resistance and elastic modulus. Examples of the non-reactive substituent include alkyl groups such as a methyl group, an ethyl group and an isopropyl group; aromatic groups such as a phenyl group; alkoxyl groups; aralkyl groups; and halogen groups such as chlorine and bromine. In addition, in order to improve the storage stability of the uncured epoxy resin composition and to improve the water absorption properties of the cured resin product, hindered amine compounds such as 4,4'-methylenebis(2,6-diethylaniline), 4,4'-methylenebis(2-ethyl-6-methylaniline) and 4,4'-methylenebis(2-isopropyl-6-methylaniline) are also suitably used.

As the aminobenzoic acid esters, trimethylene glycol di-p-aminobenzoate and neopentyl glycol di-p-aminobenzoate are preferably used. Composite materials obtained by curing with these curing agents have lower heat resistance but higher tensile elongation than those of composite materials obtained by curing with various isomers of diaminodiphenyl sulfone.

Examples of acid anhydrides include 1,2,3,6-tetrahydrophthalic anhydride, hexahydrophthalic anhydride, and 4-methylhexahydrophthalic anhydride. When these curing agents are used, the uncured resin composition has a long pot life, and a cured product having relatively well-balanced electrical properties, chemical properties, mechanical properties and the like can be obtained. The curing agent is appropriately selected depending on the intended use of the composite material.

The amount of the curing agent contained in the epoxy resin composition is an amount suitable for curing all the epoxy resins blended in the epoxy resin composition, and is appropriately adjusted depending on the types of epoxy resin and curing agent used. For example, when an aromatic diamine compound is used as the curing agent, the amount of the curing agent is preferably 25 to 65 parts by mass, more preferably 35 to 55 parts by mass, based on 100 parts by mass of the total epoxy resin amount. If it is less than 25 parts by mass or more than 65 parts by mass, the epoxy resin composition is not sufficiently cured, and the physical properties of the cured resin are likely to deteriorate.

The epoxy resin composition of the present invention indispensably contains the above-described epoxy compound and a curing agent therefor, but may contain any other component.

The epoxy resin composition of the present invention indispensably contains the above-described epoxy compound, but may contain an epoxy resin other than the epoxy compound of the present invention. As such other epoxy resin, a conventionally known epoxy resin can be used. Specifically, an epoxy resin containing an aromatic group is preferable, and an epoxy resin containing either a glycidylamine structure or a glycidyl ether structure is preferable. Further, an alicyclic epoxy resin can also be suitably used. When the epoxy compound represented by chemical formula (1) is used in combination with another epoxy resin, the content proportion of the epoxy compound represented by chemical formula (1) in the total epoxy resin contained in the epoxy resin composition is preferably 20% by mass or more, more preferably 50% by mass or more, further preferably 60 to 100% by mass.

Examples of the epoxy resin containing a glycidylamine structure include various isomers of tetraglycidyldiaminodiphenylmethane, N,N,O-triglycidyl-p-aminophenol, N,N,O-triglycidyl-m-aminophenol, N,N,O-triglycidyl-3-methyl-4-aminophenol, and triglycidylaminocresol.

Examples of the epoxy resin containing a glycidyl ether structure include bisphenol A epoxy resins, bisphenol F epoxy resins, bisphenol S epoxy resins, phenol novolac epoxy resins, and cresol novolac epoxy resins.

Further, these epoxy resins may have a non-reactive substituent in the aromatic ring structure or the like, if necessary. Examples of the non-reactive substituent include alkyl groups such as a methyl group, an ethyl group and an isopropyl group; aromatic groups such as a phenyl group; alkoxyl groups; aralkyl groups; and halogen groups such as chlorine and bromine.

The epoxy resin composition of the present invention may contain a thermoplastic resin. Examples of the thermoplastic resin include an epoxy resin-soluble thermoplastic resin and an epoxy resin-insoluble thermoplastic resin.

The epoxy resin-soluble thermoplastic resin adjusts the viscosity of the epoxy resin composition and improves the impact resistance of the obtained FRP.

The epoxy resin-soluble thermoplastic resin is a thermoplastic resin of which a part or the entirety is dissolved in the epoxy resin at a temperature at which FRP is molded or lower. Here, the matter that a thermoplastic resin is partly dissolved in the epoxy resin means that, when 10 parts by mass of a thermoplastic resin having an average particle sire of 20 to 50 µm is mixed with 100 parts by mass of the epoxy resin and stirred at 190° C. for 1 hour, the particles disappear or the size of the particles changes by 10% or more.

On the other hand, the epoxy resin-insoluble thermoplastic resin refers co a thermoplastic resin which is substantially not dissolved in the epoxy resin at a temperature at which FRP is molded or lower. It refers to a thermoplastic resin in which, when 10 parts by mass of a thermoplastic resin having an average particle size of 20 to 50 µm is mixed with 100 parts by mass of the epoxy resin and stir red at 190° C. for 1 hour, the size of the particles do not change by 10% or more. Generally, the temperature at which FRP is molded ranges from 100 to 190° C., The particle size is visually measured using a microscope, and the average particle size means an average value of particle size of 100 randomly selected particles.

When the epoxy resin-soluble thermoplastic resin is not completely dissolved, at can be dissolved in the epoxy resin by being heated in the curing process of the epoxy resin, and the viscosity of the epoxy resin composition can be increased. This makes it possible to prevent the flow of the epoxy resin composition (a phenomenon in which the resin composition flows out from the prepreg) due to the decrease in viscosity in the curing process.

The epoxy resin-soluble thermoplastic resin is preferably a resin dissolved in the epoxy resin in an amount of 80% by mass or more at 190° C.

Specific examples of the epoxy resin-soluble thermoplastic resin include polyethersulfone, polysulfone, polyetherimide, and polycarbonate. These thermoplastic resins may be used alone, or two or more thereof may be used in combination. As the epoxy resin-soluble thermoplastic resin contained in the epoxy resin composition, polyethersulfone or polysulfone having a weight average molecular weight (Mw) in the range of 8000 to 100000 as measured by gel permeation chromatography is particularly preferable. If the weight average molecular weight (Mw) is smaller than 8000, the impact resistance of the obtained FRP may be insufficient. If it is larger than 100000, the viscosity is significantly high, and the handleability may significantly deteriorate. The molecular weight distribution of the epoxy resin-soluble thermoplastic resin is preferably uniform. In particular, the polydispersity (Mw/Mn), which is the ratio of the weight average molecular weight (Mw) to the number average molecular weight (Mn), is preferably in the range of 1 to 10, more preferably in the range of 1.1 to 5.

The epoxy resin-soluble thermoplastic resin preferably has a reactive group having reactivity with the epoxy resin or a fungi tonal group that forms a hydrogen bond. Such an epoxy resin-soluble thermoplastic resin can improve the dissolution stability of the epoxy resin in the curing process. Further, toughness, chemical resistance, heat resistance and moisture heat resistance can be imparted to the FRP obtained after curing.

As the reactive group having reactivity with the epoxy resin, a hydroxyl group, a carboxylic acid group, an imino group, an amino group or the like is preferable. It is more preferable to use a hydroxyl group-terminated polyethersulfone because the obtained ISP has particularly excellent impact resistance, fracture toughness and solvent resistance.

The content of the epoxy resin-soluble thermoplastic resin contained in the epoxy resin composition is appropriately adjusted according to the viscosity. From the viewpoint of processability of the prepreg, the content of the epoxy resin-soluble thermoplastic resin is preferably 5 to 90 parts by mass, more preferably 5 to 40 parts by mass, further preferably 15 to 35 parts by mass based on 100 parts by mass of the epoxy resin contained in the epoxy resin composition. If it is less than 5 parts by mass, the impact resistance of the obtained FRP may be insufficient. When the content of the epoxy resin-soluble thermoplastic resin is high, the viscosity is remarkably high, and the handleability of the prepreg may remarkably deteriorate.

The epoxy resin-soluble thermoplastic resin preferably contains a reactive aromatic oligomer having an amine terminal Group (hereinafter, also simply referred to as "aromatic oligomer").

The epoxy resin composition has a high molecular weight due to a curing reaction between the epoxy resin and the curing agent during heat curing. The two-phase region expands due to the high molecular weight, the aromatic oligomer dissolved in the epoxy resin composition causes a reaction-induced phase separation. By this phase separation, a two-phase structure of resin in which the cured epoxy resin and the aromatic oligomer are co-continuous is formed in the matrix resin. Further, since the aromatic oligomer has an amine terminal group, a reaction with the epoxy resin also occurs. Since each phase in this co-continuous two-phase structure is firmly bonded to each other, the solvent resistance is also improved.

This co-continuous structure absorbs an external impact on the cured resin and suppresses crack propagation. As a result, the cured resin produced by using the epoxy, resin composition containing the reactive aromatic oligomer having an amine terminal group has high impact resistance and fracture toughness.

As the aromatic oligomer, a known polysulfone having an amine terminal group or a known polyethersulfone having an amine terminal group can be used. The amine terminal group is preferably a primary amine ($-NH_2$) terminal group.

The aromatic oligomer blended in the epoxy resin composition preferably has a weight average molecular weight of 8000 to 40,000 as measured by gel permeation chromatography. When the weight average molecular weight is less than 8000, the toughness improving effect of the matrix resin is low. On the other hand, when the weight average molecular weight exceeds 40000, the viscosity of the resin composition becomes too high, and processing problems such as difficulty in impregnating the reinforcing fiber layer with the resin composition are likely to occur.

The form of the epoxy resin-soluble thermoplastic resin is not particularly limited, but is preferably in the form of particles. The particulate epoxy resin-soluble thermoplastic resin can be uniformly blended in the resin composition. In addition, the moldability of the obtained prepreg can be improved.

The average particle size of the epoxy resin-soluble thermoplastic resin is preferably 1 to 50 µm, particularly preferably 3 to 30 µm. If it is less than 1 µm, the viscosity of the epoxy resin composition significantly increases. Therefore, it may be difficult to add a sufficient amount of the epoxy resin-soluble thermoplastic resin to the epoxy resin composition. If it exceeds 50 µm, it may be difficult to obtain a sheet having a uniform thickness when the epoxy resin composition is processed into a sheet. In addition, the rate of dissolution in the epoxy resin decreases, and the obtained FRP becomes non-uniform. Thus, such an amount is not preferable.

The epoxy resin composition may contain an epoxy resin-insoluble the plastic resin in addition to the epoxy resin-soluble thermoplastic resin. The epoxy resin-insoluble thermoplastic resin and a part of the epoxy resin-soluble thermoplastic resin (the epoxy resin-soluble thermoplastic resin remaining undissolved in the cured matrix resin) are in a state in which the particles thereof are dispersed in the cured resin. These particles suppress the propagation of impact on the cured resin. As a result, the impact resistance of the obtained cured resin is improved.

Examples of the epoxy resin-insoluble thermoplastic resin include polyamide, polyacetal, polyphenylene oxide, polyphenylene sulfide, polyester, polyamideimide, polyimide, polyetherketone, polyetheretherketone, polyethylenenaphthalate, polyethernitrile, and polybenzimidazole. Among these, polyamide, polyamideimide, and polyimide are preferable because they have high toughness and heat resistance. Polyamide and polyimide are particularly excellent in the toughness improving effect on the cured resin. These thermoplastic resins may be used alone, or two or more thereof may be used in combination. Moreover, copolymers of these thermoplastic resins can also be used.

In particular, an amorphous polyimide or a polyamide such as nylon 6 (registered trademark) (polyamide obtained by a ring-opening polycondensation reaction of caprolactam), nylon 11 (polyamide obtained by a ring-opening polycondensation reaction of undecanlactam), nylon 12 (polyamide obtained by a ring-opening polycondensation reaction of lauryllactam), nylon 1010 (polyamide obtained by a copolymerization reaction of sebacic acid and 1,10-decanediamine) or amorphous nylon (nylon also referred to as transparent nylon, which does not cause polymer crystallization or has an extremely slow polymer crystallization rate) is used, thereby making it possible to particularly improve the heat resistance of the obtained cured resin.

The content of the epoxy resin-insoluble thermoplastic resin in the epoxy resin composition is appropriately adjusted according to the viscosity of the epoxy resin composition. The content is preferably 5 to 50 parts by mass, more preferably 10 to 45 parts by mass, further preferably 20 to 40 parts by mass based on 100 parts by mass of the epoxy resin contained in the epoxy resin composition. If it is less than 5 parts by mass, the impact resistance of the obtained cured resin may be insufficient. If it exceeds 50 parts by mass, the viscosity of the epoxy resin composition increases and the handleability decreases.

The preferable average particle size and form of the epoxy resin-insoluble thermoplastic resin are the same as those of the epoxy resin-soluble thermoplastic resin.

The epoxy resin composition of the present invention may contain conductive particles, a flame retardant, an inorganic filler, and/or an internal mold release agent.

Examples of the conductive particles include conductive polymer particles such as polyacetylene particles, polyaniline particles, polypyrrole particles, polythiophene particles, polyisothianaphthene particles and polyethylenedioxythiophene particles; carbon particles; carbon fiber particles; metal particles; and particles in which a core material made of an inorganic material or organic material is coated with a conductive substance.

Examples of the flame retardant include phosphorus-based flame retardants. The phosphorus-based flame retardant is not particularly limited as long as it contains a phosphorus atom in the molecule, and examples thereof include organic phosphorus compounds such as phosphoric acid ester, condensed phosphoric acid ester, phosphazene compound, and polyphosphate, and red phosphorus.

Examples of the inorganic filler include aluminum borate, calcium carbonate, silicon carbonate, silicon nitride, potassium titanate, basic magnesium sulfate, zinc oxide, graphite, calcium sulfate, magnesium borate, magnesium oxide, and silicate minerals. In particular, it is preferable to use a silicate mineral. Specific examples of the silicate mineral include THIXOTROPIC AGENT DT 5039 (manufactured by Huntsman Japan K.K.).

Examples of the internal mold release agent can include metal soaps, vegetable waxes such as polyethylene wax and carnauba wax, fatty acid ester mold release agents, silicone oils, animal waxes, and fluorine-based nonionic surfactants. The amount of such an internal mold release agent to be blended is preferably 0.1 to 5 parts by mass, more preferably 0.2 to 2 parts by mass based on 100 parts by mass of the epoxy resin. Within this range, the mold release effect from the mold is preferably exhibited.

Specific examples of the internal mold release agent include "MOLD WIZ (registered trademark)" INT1846 (manufactured by AXEL PLASTICS RESEARCH LABORATORIES INC.), Licowax S, Licowax P, Licowax OP, Licowax PE190, and Licowax PR) (manufactured by Clariant Japan K.K.), and stearyl stearate (SL-900A; manufactured by RIKEN Vitamin Co., Ltd.).

The epoxy resin composition of the present invention can be produced by mixing an epoxy resin, a curing agent, and, if necessary, any other component. The order of mixing these components is not limited.

The method for producing the epoxy resin composition is not particularly limited, and any conventionally known method may be used. A temperature in the range of 40 to 120° C. can be exemplified as the mixing temperature. If it exceeds 120° C., the curing reaction partially proceeds, and the impregnation property of the obtained epoxy resin composition into the reinforcing fiber base material layer may be lowered, and the storage stability of the obtained epoxy resin composition and the prepreg produced by using the epoxy resin composition may deteriorate. If it is less than 40° C., the viscosity of the epoxy resin composition is high, and the mixing may be substantially difficult. It is preferably in the range of 50 to 100° C., more preferably in the range of 50 to 90° C.

A conventionally known mixing machine device can be used. Specific examples of the mixing machine device include a roll mill, a planetary mixer, a kneader, an extruder, a Banbury mixer, a mixing vessel equipped with a stirring blade, and a horizontal mixing tank. The components can be mixed in the air or in an atmosphere of an inert gas. When the mixing is performed in the air, an atmosphere in which the temperature and humidity are controlled is preferable. The mixing is preferably performed, for example, at a temperature controlled to a constant temperature of 30° C. or less or in a low humidity atmosphere having a relative humidity of 50% RH or less, although not particularly limited.

4. Cured Resin

The cured resin of the present invention is a cured product obtained by curing the above-described epoxy resin composition.

The curing reaction is appropriately determined depending on the epoxy resin and curing agent contained in the epoxy resin composition, and is usually carried out by heating at 20 to 250° C. for 0.5 hours or more.

The cured resin of the present invention is characterized by having a low water absorption. The water absorption as used herein refers to a mass increase rate after storage for 24 hours under the conditions of 121° C. and 100% RH. The water absorption is preferably less than 5.0% by mass, more preferably less than 4.0% by mass, further preferably less than 3.5% by mass. The lower limit of the water absorption is not particularly limited, but is usually 0.5% by mass or more. When the water absorption is 5.0% by mass or more, the strength of the cured resin molded into a thin plate may easily decrease.

The cured resin of the present invention has a flexural modulus of preferably 3.0 GPa or more, more preferably 3.5 to 30 GPa, further preferably 4.0 to 20 GPa, as measured according to the JIS K7171 method. If it is less than 3.0 GPa, the properties of the obtained cured resin and fiber-reinforced composite material tend to deteriorate.

5. Prepreg

The prepreg of the present invention contains a reinforcing fiber base material and the above-described epoxy resin composition of the present invention impregnated into the reinforcing fiber base material.

The prepreg of the present invention is a prepreg in which the epoxy resin composition is impregnated into a part or the entirety of a reinforcing fiber base material. The content rate of the epoxy resin composition in the entire prepreg is preferably 15 to 60% by mass based on the total mass of the prepreg. When the resin content rate is less than 15% by mass, voids or the like may be generated in the obtained fiber-reinforced composite material, and the mechanical properties may deteriorate. If the resin content rate exceeds 60% by mass, the reinforcing effect obtained by the reinforcing fibers may be insufficient, and the mechanical properties relative to the mass may be substantially low. The resin content rate is preferably 20 to 55% by mass, more preferably 25 to 50% by mass.

The reinforcing fiber base material used in the present invention is not particularly limited, and examples thereof include carbon fibers, glass fibers, aramid fibers, silicon carbide fibers, polyester fibers, ceramic fibers, alumina fibers, boron fibers, metal fibers, mineral fibers, rock fibers, and slug fibers.

Among these reinforcing fibers, carbon fibers, glass fibers, and aramid fibers are preferable. Carbon fibers are more preferable because a fiber-reinforced composite material having good specific strength and specific elastic modulus, being lightweight and having high strength can be obtained. Polyacrylonitrile (PAN)-based carbon fibers are particularly preferable because they have excellent tensile strength.

When PAN-based carbon fibers are used as the reinforcing fibers, the tensile elastic modulus thereof is preferably 100 to 600 GPa, more preferably 200 to 500 GPa, particularly preferably 230 to 450 GPa. The tensile strength is preferably 2000 to 10000 MPa, more preferably 3000 to 8000 MPa. The diameter of the carbon fibers is preferably 4 to 20 µm, more preferably 5 to 10 µm. The use of such carbon fibers makes it possible to improve the mechanical properties of the obtained fiber-reinforced composite material.

The reinforcing fibers are preferably formed into a sheet and used. Examples of the reinforcing fiber sheet can include sheets in which a large number of reinforcing fibers are aligned in one direction, bidirectional woven fabrics such as plain weave and twill weave, multi-axis woven fabrics, non-woven fabrics, mats, knits, braids, and papers made from reinforcing fibers. Among these, it is preferable to use a sheet in which reinforcing fibers as continuous fibers are formed into a sheet such as a unidirectionally aligned sheet, a bidirectional woven fabric, or a multi-axis woven fabric base material because a fiber-reinforced composite material having more excellent mechanical properties can be obtained. The thickness of the sheet-shaped reinforcing fiber base material is preferably 0.01 to 3 mm, more preferably 0.1 to 1.5 mm.

The method for producing the prepreg of the present invention is not particularly limited, and any conventionally known method can be adopted. Specifically, the hot melt method and the solvent method can be preferably adopted.

The hot melt method is a method in which a resin composition is applied in the form of a thin film onto a release paper to form a resin composition film, and the resin composition film is laminated on a reinforcing fiber base material and heated under pressure to impregnate the resin composition into the reinforcing fiber base material layer.

The method for forming the resin composition into a resin composition film is not particularly limited, and any conventionally known method can be used. Specifically, a resin composition film can be obtained by casting a resin composition on a support such as a release paper or a film using a die for extruder, an applicator, a reverse roll coater, a comma coater, or the like. The resin temperature at the time of producing the film is appropriately determined according to the composition and viscosity of the resin composition. Specifically, the same temperature condition as the mixing temperature in the method for producing the epoxy resin composition described above is preferably used. The resin composition may be impregnated into the reinforcing fiber base material layer once or in a plurality of times.

The solvent method is a method in which an epoxy resin composition is formed into a varnish using an appropriate solvent, and the varnish is impregnated into a reinforcing fiber base material layer.

Among these conventional methods, the prepreg of the present invention can be suitably produced by the hot melt method that does not use a solvent.

When the epoxy resin composition film is impregnated into the reinforcing fiber base material layer by the hot melt method, the impregnation temperature is preferably in the range of 50 to 120'C. When the impregnation temperature is less than 50° C., the viscosity of the epoxy resin is high, and the epoxy resin may not be sufficiently impregnated into the reinforcing fiber base material layer. When the impregnation temperature exceeds 120° C., the curing reaction of the epoxy resin composition proceeds, and the storage stability of the obtained prepreg may decrease, and the drape property may decrease. The impregnation temperature is more preferably 60 to 110° C., particularly preferably 70 to 100° C.

The impregnation pressure when the epoxy resin composition film is impregnated into the reinforcing fiber base material layer by the hot melt method is appropriately determined in consideration of the viscosity and resin flow of the resin composition.

The specific impregnation pressure is 0.01 to 250 N/cm, preferably 0.1 to 200 N/cm.

6. Fiber-Reinforced Composite Material (FRP)

The fiber-reinforced composite material of the present invention contains the cured resin of the present invention and a reinforcing fiber base material. The fiber-reinforced composite material is produced by curing the reinforcing fiber base material and the epoxy resin composition of the present invention in a composited state. The method for producing the fiber-reinforced composite material is not particularly limited, and the fiber-reinforced composite, material may be produced using a prepreg in which the reinforcing fiber base material and the epoxy resin composition are composited in advance. Further, as exemplified by the resin transfer molding method (RTM method), the hand layup method, the filament winding method, and the pultrusion method, the reinforcing fiber base material and the epoxy resin composition may be composited at the same time as molding.

Examples of the method for producing FRP using the prepreg of the present invention include known molding methods such as autoclave molding and press molding.

(6-1) Autoclave Molding Method

As the method for producing FRP of the present invention, an autoclave molding method is preferably used. The autoclave molding method is a method in which a prepreg and a film bag are sequentially laid on the lower mold of a mold, the prepreg is sealed between the lower mold and the film bag, and the space formed by the lower mold and the film bag is evacuated, and, at the same time, heat and pressure are applied using an autoclave molding apparatus. The molding conditions are preferably such that the temperature increase rate is set to 1 to 50° C./min, and that heat and pressure are applied at 0.2 to 0.7 MPa and 130 to 180° C. for 10 to 300 minutes.

(6-2) Press Molding Method

As the method for producing FRP of the present invention, a press molding method is preferably used. The production of FRP by the press molding method is carried out by heating and pressurizing the prepreg of the present invention or a preform formed by laminating the prepreg of the present invention using a mold. The mold is preferably preheated to the curing temperature.

The temperature of the mold during press molding is preferably 150 to 210° C. When the molding temperature is 150° C. or higher, a sufficient curing reaction can be caused and FRP can be obtained with high productivity. Further, when the molding temperature is 210° C. or lower, the resin viscosity does not become too low, and excessive flow of the resin in the mold can be suppressed. As a result, high-quality FRP can be obtained because the outflow of resin from the mold and the meandering of fibers can be suppressed.

The pressure during molding is 0.05 to 2 MPa, preferably 0.2 to 2 MPa. When the pressure is 0.05 MPa or more, an appropriate flow of the resin can be obtained, and generation of voids and poor appearance can be prevented. In addition, since the prepreg is sufficiently adhered to the mold, it is possible to produce FRP having a good appearance. When the pressure is 2 MPa or less, the resin does not flow more than necessary, so that the appearance of the obtained FRP is unlikely to deteriorate. In addition, since the mold is not loaded more than necessary, the mold is unlikely to be deformed.

The molding time is preferably 1 to 8 hours.

(6-3) Resin Transfer Molding Method (RTM)

It is also preferable to use the RTM method from the viewpoint of efficiently obtaining a fiber-reinforced composite material having a complicated shape. Here, the RTM method means a method in which a liquid epoxy resin composition is impregnated into a reinforcing fiber base material arranged in a mold and cured to produce a fiber-reinforced composite material.

In the present invention, the mold used in the RTM method may be a closed mold made of a rigid material, or an open mold made of a rigid material and a flexible film (bag) can also be used. In the latter case, the reinforcing fiber base material can be placed between the open mold made of the rigid material and the flexible film. As the rigid material, various existing materials such as metals such as steel and aluminum, fiber-reinforced plastic (FRP), wood, and gypsum are used. Polyamide, polyimide, polyester, fluororesin, silicone resin or the like is used as the material of the flexible film.

When a closed mold made of a rigid material is used in the RTM method, usually, mold closing is performed by pressurization, and then the epoxy resin composition is pressurized and injected. At this time, it is also possible to provide a suction port separately from an injection port and connect it to a vacuum pump for suction. It is also possible to perform suction and inject the epoxy resin composition only with atmospheric pressure without using a special pressurizing means. This method can be preferably used because a large-sized member can be produced by providing a plurality of suction ports.

In the RTM method, when an open mold made of a rigid material and a flexible film are used, suction may be performed and the epoxy resin may be injected only with atmospheric pressure without using a special pressurizing means. It is effective to use a resin diffusion medium in order to realize good impregnation by injection only with atmospheric pressure. Further, it is preferable to apply a gel coat to the surface of the rigid material prior to the placement of the reinforcing fiber base material.

In the RTM method, the epoxy resin composition is impregnated into the reinforcing fiber base material and then heat-cured. As the mold temperature during heat curing, a temperature higher than the mold temperature at the time of injecting the epoxy resin composition is usually selected. The mold temperature during heat curing is preferably 80 to 200° C. The heat curing time is preferably 1 minute to 20 hours. After the heat curing is completed, the mold is removed to take out the fiber-reinforced composite material. Then, the obtained fiber-reinforced composite material may be heated at a higher temperature for post-curing. The post-curing temperature is preferably 150 to 200° C., and the time is preferably 1 minute to 4 hours.

The impregnation pressure when the reinforcing fiber base material is impregnated with the epoxy resin composition by the RTM method is appropriately determined in consideration of the viscosity and resin flow of the resin composition.

The specific impregnation pressure is 0.001 to 10 MPa, preferably 0.01 to 1 MPa. When the fiber-reinforced composite material is obtained by the RTM method, the viscosity of the epoxy resin composition at 100° C. is preferably less than 5000 mPa·s, more preferably 1 to 1000 mPa·s.

EXAMPLES

Hereinafter, the present invention will be described in more detail by way of Examples, but is not limited to the Examples. The components and test methods used in the Examples and Comparative Examples will be described below.

[Evaluation Methods]

(1) Viscosity

The viscosity of an epoxy resin was measured using a rheometer ARES-RDA manufactured by TA Instruments. Parallel plates having a diameter of 25 mm were used, the thickness of the epoxy resin between the parallel plates was set to 0.5 mm, and the viscosity thereof was measured up to 180° C. at a temperature increase rate of 2° C./min. under the condition of an angular velocity of 10 radians/sec, so that the viscosity at 50° C. was determined from the temperature viscosity curve. An epoxy resin solid at room temperature was once exposed to a temperature not lower than the melting point and molten, and the measurement was started in a supercooled state.

(2) Flexural Modulus

A test was conducted according to the JIS K7171 method. The dimensions of a resin test piece at that time were set to 80 mm×10 mm×4 mm. The distance L between the fulcrums was set to 16×h (thickness), and a bending test was conducted at a test speed of 2 mm/min. to measure the flexural modulus.

(3) Water Absorption

A pressure cooker (HASTEST PC-422R8 manufactured by ESPEC Corporation) was used to subject the resin test piece prepared under the conditions of 121° C. and 24 hours to water absorption treatment. The water absorption was calculated according to the following formula (1).

Water absorption=$(W_2-W_1)/W_1 \times 100$    Formula (1)

$W_1$: Weight of test piece before water absorption treatment $W_2$: Weight of test piece after water absorption treatment (4) Purity of Epoxy Compound High-performance liquid chromatography (HPLC) measurement was performed under the following conditions so that the purity of an epoxy compound was measured from the peak area fraction.

Column: Inertsil ODS-3V (4.6 φ×250 mm)
Temperature: 40° C.
Mobile phase: Acetonitrile/10 mM ammonium formate
Flow rate: 1 mL/min
Detection wavelength: 254 nm.

[Component]
(Epoxy Compound)

Synthesis Example 1

An epoxy compound of the following chemical formula (3) was synthesized.

[Chemical Formula 7]

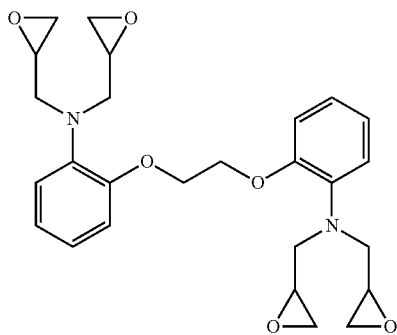

Chemical Formula (3)

The method for synthesizing this epoxy compound is as follows.

In a four-necked flask equipped with a thermometer, a dropping funnel, a condenser and a stirrer, 100 g (0.41 mol) of 1,2-bis(2-aminophenoxy)ethane, 250.0 g of toluene, and 25.0 g of distilled water were charged under a nitrogen atmosphere. To this mixture, 454.5 g (4.91 mol) of epichlorohydrin was added, and the mixture was stirred at 80° C. for 12 hours to complete the addition reaction, so that. N,N,N′,N′-tetrakis(2-hydroxy-3-chloropropyl)-1,2-bis(2-aminophenoxy)ethane was obtained. Subsequently, the temperature inside the flask was lowered to 30° C., 4.2 g (12.3 mmol) of tetrabutylammonium hydrogensulfate was then added, 204.7 g (2.46 mol) of a 48% aqueous NaOH solution was added dropwise thereto over 40 minutes, and the solution mixture was stirred for 3 hours. To the obtained reaction solution, 450 of distilled water was added, and an organic layer was separated. The obtained organic layer was washed once with saturated brine and once with distilled water, dehydrated with sodium sulfate, and then filtered, and the filtrate was concentrated to yield 187.7 g of a crude product. The obtained crude product was subjected to silica gel chromatography to yield 79.8 g of a pale yellow viscous liquid.

The purity of the epoxy compound of the above chemical formula (3), as the main product, was 97.8% (HPLC area %). The viscosity at 50° C. was 1.1 Pa·s.

Synthesis Example 2

An epoxy compound of the following chemical formula (4) was synthesized.

[Chemical Formula 8]

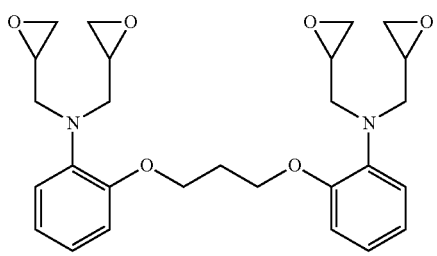

Chemical Formula (4)

The method for synthesizing this epoxy compound is as follows.

In a four-necked flask equipped with a thermometer, a dropping funnel, a condenser and a stirrer, 106.6 g (0.41 mol) of 1,3-bis(2-aminophenoxy)propane, 266.5 g of toluene, and 26.65 g of distilled water were charged under an argon atmosphere. To this mixture, 458.1 g (4.95 mol) of epichlorohydrin was added, and the mixture was stirred at 80° C. for 24 hours to complete the addition reaction, so that N,N,N′,N′-tetrakis(2-hydroxy-3-chloropropyl)-1,3-bis(2-aminophenoxy)propane was obtained. Subsequently, the temperature inside the flask was lowered to 40° C., 4.2 g (12.3 mmol) of tetrabutylammonium hydrogensulfate was then added, and 206.3 g (2.48 mol) of a 48% aqueous NaOH solution was added dropwise thereto over 20 minutes. The internal temperature was increased to 50° C., and the solution mixture was then stirred for 4 hours. To the obtained reaction solution, 400 ml of distilled water and 400 ml of toluene were added, and an organic layer was separated. The obtained organic layer was washed twice with 5% brine, dehydrated with sodium sulfate, and then filtered, and the filtrate was concentrated to yield 221.5 g of a crude product. The obtained crude product was subjected to silica gel chromatography to yield 97.9 g of a pale brown viscous liquid.

The purity of the epoxy compound of the above chemical formula (4), as the main product, was 98.9% (HPLC area %). The viscosity at 50° C. was 0.6 Pa·s.

Comparative Synthesis Example 1

An epoxy compound of the following chemical formula (5) was synthesized.

[Chemical Formula 9]

Chemical Formula (5)

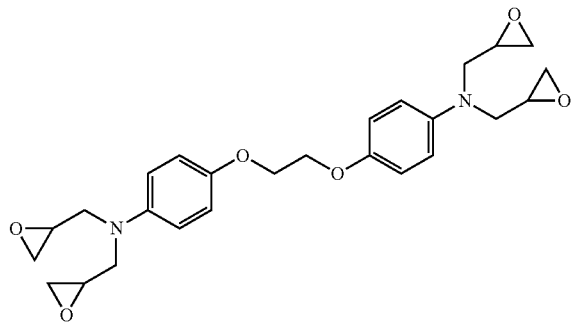

The method for synthesizing this epoxy compound is as follows.

In a four-necked flask equipped with a thermometer, a dropping funnel, a condenser and a stirrer. 100.0 g (0.41 mol) of 1,2-bis(4-aminophenoxy)ethane, 250.0 g of toluene, and 25.0 g of distilled water were charged under a nitrogen atmosphere. To this mixture, 454.5 g (4.91 mol) of epichlorohydrin was added, and the mixture was stirred at 80° C. for 8 hours to complete the addition reaction, so that N,N,N',N'-tetrakis(2-hydroxy-3-chloropropyl)-1,2-bis(4-aminophenoxy)ethane was obtained. Subsequently, the temperature inside the flask was lowered to 30° C., 4.2 g (12.3 nmol) of tetrabutylammonium hydrogensulfate was then added, 204.7 g (2.46 mol) of a 48% aqueous NaOH solution was added dropwise thereto over 60 minutes, and the solution mixture was stirred for 2 hours. To the obtained reaction solution, 450 mL of distilled water was added, and an organic layer was separated. The obtained organic layer was washed twice with saturated brine, dehydrated with sodium sulfate, and then filtered, and the filtrate was concentrated to yield 179.0 g of a crude product. The obtained crude product was subjected to silica gel chromatography to yield 136.2 g of a yellow solid.

The purity of the epoxy compound of the above chemical formula (5), as the main product, was 97.3% (HPLC area %). The viscosity at 50° C. was 2.1 Pa·s.

Comparative Synthesis Example 2

An epoxy compound of the following chemical formula (6) was synthesized.

[Chemical Formula 10]

Chemical Formula (6)

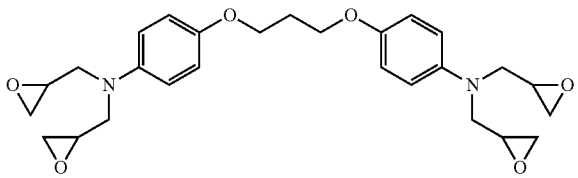

The method for synthesizing this epoxy compound is as follows.

In a four-necked flask equipped with a thermometer, a dropping funnel, a condenser and a stirrer, 200.0 g (0.77 mol) of 1,3-bis(4-aminophenoxy)propane, 502.0 g of toluene, and 50.2 g of distilled water were charged under an argon atmosphere. To this mixture, 860.0 g (9.30 mol) of epichlorohydrin was added, and the mixture was stirred at 80° C. for 15 hours to complete the addition reaction, so that N,N,N',N'-tetrakis(2-hydroxy-1-chloropropyl)-1,3-bis(4-aminophenoxy) propane was obtained. Subsequently, the temperature inside the flask was lowered to 30° C., 7.82 g (23.0 mmol) of tetrabutylammonium hydrogensulfate was then added, 388.0 g (4.66 mol) of a 48% aqueous NaOH solution was added dropwise thereto over 20 minutes, and the solution mixture was stirred for 4 hours. To the obtained reaction solution, 600 ml of distilled water and 1100 of toluene were added, and an organic layer was separated. The obtained organic layer was washed twice with distilled water and then 0.5% brine, dehydrated with sodium sulfate, and then filtered, and the filtrate was concentrated to yield 408.0 g of a crude product. The obtained crude product was subjected to silica gel chromatography to yield 189.0 g of a pale brown viscous liquid.

The purity of the epoxy compound of the above chemical formula (6), as the main product, was 95.6% (HPLC area %). The viscosity at 50° C. was 0.9 Pa·s.

Tetraglycidyl-4,4'-diaminodiphenylmethane (Araidite MY721 manufactured by Huntsman Corporation, viscosity at 50° C.: 3.3 Pa·s, hereinafter abbreviated as "TGDDM")

(Curing Agent)

3,3'-Diaminodiphenyl sulfone (manufactured by Konishi Chemical Industry Co., Ltd., hereinafter abbreviated as "3,3'-DDS")

Examples 1 and 2 and Comparative Examples 1 to 3

A curing agent was added to each of the epoxy resins at the ratio shown in Table 1 and mixed at 40° C. for 30 minutes using a stirrer to prepare an epoxy resin composition. In the composition shown in Table 1, the glycidyl group of the epoxy resin and the amino group of the curing agent are equivalent in amount. This epoxy resin composition was defoamed in vacuum and then injected into a silicone resin mold set to have a thickness of 4 mm by a silicone resin spacer having a thickness of 4 mm. It was cured at a temperature of 180° C. for 2 hours to yield a cured resin product having a thickness of 4 mm. Each of the epoxy resins and each of the cured resin products were evaluated according to the above evaluation methods, and the results are shown in Table 1.

TABLE 1

|  |  |  | Example 1 | Example 2 | Comparative Example 1 | Comparative Example 2 | Comparative Example 3 |
|---|---|---|---|---|---|---|---|
| Resin composition | Epoxy resin A | Synthesis Example 1 | 100 | 0 | 0 | 0 | 0 |
|  |  | Synthesis Example 2 | 0 | 100 | 0 | 0 | 0 |
|  | Other epoxy resins | TGDDM | 0 | 0 | 100 | 0 | 0 |
|  |  | Synthesis Example 3 | 0 | 0 | 0 | 100 | 0 |
|  |  | Synthesis Example 4 | 0 | 0 | 0 | 0 | 100 |
|  | Curing agent | 3,3'-DDS | 51.2 | 49.6 | 56.3 | 52.9 | 50.4 |
| Property of epoxy resin | Viscosity at 50° C. (Pa · s) |  | 1.1 | 0.6 | 3.3 | 2.1 | 0.9 |
| Property of cured resin product | Flexural modulus (GPa) |  | 4.3 | 4.2 | 4.2 | 3.9 | 3.5 |
|  | Water absorption (%) |  | 3.2 | 2.9 | 3.9 | 4.9 | 4.0 |

The epoxy compounds of Examples 1 and 2 had a low viscosity and thus were excellent in handleability, and can provide cured resin products having a high elastic modulus and a low water absorption. On the other hand, in Comparative Examples 1 to 3 each using the epoxy compound having no structure specified in the present invention, various physical properties were lowered.

The invention claimed is:

1. An epoxy compound represented by the following chemical formula (1)

[Chemical Formula 1]

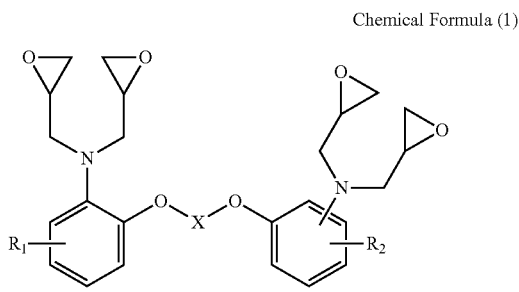

Chemical Formula (1)

wherein X is a C1-10 aliphatic hydrocarbon group, and $R_1$ and $R_2$ each independently represent one selected from the group consisting of a hydrogen atom, an aliphatic hydrocarbon group, an aromatic group, an alkoxy group, and a halogen atom.

2. The epoxy compound according to claim 1, which is represented by the following chemical formula (2)

[Chemical Formula 2]

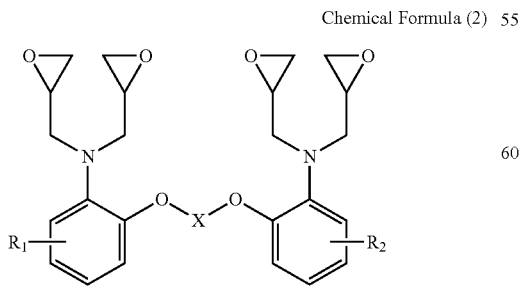

Chemical Formula (2)

wherein X is a C1-10 aliphatic hydrocarbon group, and $R_1$ and $R_2$ each independently represent one selected from the group consisting of a hydrogen atom, an aliphatic hydrocarbon group, an aromatic group, an alkoxy group, and a halogen atom.

3. The epoxy compound according to claim 2, wherein X is a linear aliphatic chain group.

4. The epoxy compound according to claim 1, wherein X is a linear aliphatic chain group.

5. An epoxy resin comprising the epoxy compound according to claim 1 in an area ratio of 50% or more in HPLC measurement.

6. An epoxy resin composition comprising at least:
the epoxy compound according to claim 1; and
a curing agent.

7. A cured resin product obtained by curing the epoxy resin composition according to claim 6.

8. A fiber-reinforced composite material comprising:
the cured resin product according to claim 7; and
a reinforcing fiber base material.

9. A prepreg including:
a reinforcing fiber base material; and
the epoxy resin composition according to claim 6, which is impregnated into the reinforcing fiber base material.

10. The prepreg according to claim 9, wherein the reinforcing fiber base material is a reinforcing fiber base material made of carbon fibers.

11. A method for producing the prepreg according to claim 9, including impregnating the epoxy resin composition into the reinforcing fiber base material.

12. A method for producing a fiber-reinforced composite material comprising (i) a cured resin product obtained by curing the epoxy resin composition according to claim 6, and (ii) a reinforcing fiber base material,
the method including impregnating the epoxy resin composition into the reinforcing fiber base material and curing the epoxy resin composition.

13. A method for producing a fiber-reinforced composite material comprising (i) a cured resin product obtained by curing the epoxy resin composition according to claim 6, and (ii) a reinforcing fiber base material,
the method including curing a prepreg including (A) the reinforcing fiber base material, and (B) the epoxy resin composition, which is impregnated into the reinforcing fiber base material.

\* \* \* \* \*